(12) United States Patent
Balasubramanian

(10) Patent No.: US 6,833,246 B2
(45) Date of Patent: Dec. 21, 2004

(54) POLYNUCLEOTIDE SEQUENCING

(75) Inventor: Shankar Balasubramanian, Cambridge (GB)

(73) Assignee: Solexa, Ltd., London (GB)

( * ) Notice: Subject to any disclaimer, the term of this patent is extended or adjusted under 35 U.S.C. 154(b) by 71 days.

(21) Appl. No.: 10/113,221

(22) Filed: Mar. 29, 2002

(65) Prior Publication Data

US 2003/0013101 A1 Jan. 16, 2003

Related U.S. Application Data

(63) Continuation of application No. PCT/GB00/03734, filed on Sep. 29, 2000.

(30) Foreign Application Priority Data

Sep. 29, 1999 (GB) .............................................. 9923084
Jan. 31, 2000 (GB) .............................................. 0002216

(51) Int. Cl.$^7$ ........................... C12G 1/68; C12P 19/34; C07H 21/02
(52) U.S. Cl. .......................... 435/6; 435/91.1; 435/91.2; 535/23.1; 535/24.3; 535/24.31; 535/24.33
(58) Field of Search .......................... 435/6, 91.1, 91.2; 536/24.3, 24.31, 24.33; 356/301, 302, 303

(56) References Cited

U.S. PATENT DOCUMENTS 5,302,509 A * 4/1994 Cheeseman ..................... 435/6
6,245,507 B1 * 6/2001 Bogdanov ....................... 435/6
6,555,349 B1 * 4/2003 O'Donnell ................. 435/91.2

FOREIGN PATENT DOCUMENTS

WO   WO00/06770   2/2000   ............ C12Q/1/68

OTHER PUBLICATIONS

Jacobs, et al. "*Combinatorial Chemistry–Applications of Light–directed Chemical Synthesis*", Trends in Biotechnology (1994) 12:19–26.

Stimpson, et al. "*Real–Time Detection of DNA Hybridization and Melting on Oligonucleotide Arrays by Using Optical Wave Guides*", PNAS (1995) 92:6379–6383.

* cited by examiner

*Primary Examiner*—Jeffrey Fredman
(74) *Attorney, Agent, or Firm*—Klauber & Jackson

(57) ABSTRACT

The invention relates to the sequencing of a target polynucleotide sequence, immobilized on a solid support, using the polymerase reaction to extend a suitable primer and characterizing the sequential addition of labelled bases. The present invention further relates to the presence of a polymerase enzyme that retains a 3' to 5' exonuclease function, which is induced to remove an incorporated labelled base after detection of incorporation. A corresponding non-labelled base may then be incorporated into the complementary strand to allow further sequence determinations to be made. Repeating the procedure allows the sequence of the complement to be identified, and thereby the target sequence.

7 Claims, 1 Drawing Sheet ns to be made.
POLYNUCLEOTIDE SEQUENCING

FIELD OF THE INVENTION

This invention relates to the sequencing of polynucleotides. In particular, this invention discloses methods for determining the sequence of polynucleotides arrayed on a solid support.

BACKGROUND TO THE INVENTION

Advances in the study of molecules have been led, in part, by improvement in technologies used to characterize the molecules or their biological reactions. In particular, the study of the nucleic acids DNA and RNA has benefited from developing technologies used for sequence analysis and the study of hybridization events.

An example of the technologies that have improved the study of nucleic acids, is the development of fabricated arrays of immobilized nucleic acids. These arrays consist typically of a high-density matrix of polynucleotides immobilized onto a solid support material. Fodor et al, Trends in Biotechnology (1994) 12:19–26, describes ways of assembling the nucleic acids using a chemically sensitized glass surface protected by a mask, but exposed at defined areas to allow attachment of suitably modified nucleotide phosphoramidites. Fabricated arrays may also be manufactured by the technique of "spotting" known polynucleotides onto a solid support at predetermined positions (e.g. Stimpson et al, PNAS (1995) 92:6379–6383).

A further development in array technology is the attachment of the polynucleotides to the solid support material to form single molecule arrays. Arrays of this type are disclosed in WO-A-00/06770. The advantage of these arrays is that reactions can be monitored at the single molecule level and information on large numbers of single molecules can be collated from a single reaction.

For DNA arrays to be useful, the sequences of the molecular must be determined. U.S. Pat. No. 5,302,509 discloses a method to sequence polynucleotides immobilized on a solid support. The method relies on the incorporation of 3-blocked bases A, G, C and T having a different fluorescent label to the immobilized polynucleotide, in the presence of DNA polymerase. The polymerase incorporates a base complementary to the target polynucleotide, but is prevented from further addition by the 3'-blocking group. The label of the incorporated base can then be determined and the blocking group removed by chemical cleavage to allow further polymerisation to occur. However, the need to remove the blocking groups in this manner is time-consuming and must be performed with high efficiency.

Similarly, EP-A-0640146 discloses a potymerisation-based technique for sequencing DNA. The technique again requires removal of a blocking group prior to subsequent incorporation of nucleotides.

SUMMARY OF THE INVENTION

In the general method of the invention, a target polynucleotide sequence can be determined by generating its complement using the potymerase reaction to extend a suitable primer, and characterizing the successive incorporation of bases that generate the complement. The target sequence is, typically, immobilized on a solid support. Each of the different bases A, T, G or C is then brought, by sequential addition, into contact with the target, and any incorporation events detected via a suitable label attached to the base. In contrast to the prior art methods, the present invention requires the presence of a polymerase enzyme that retains a 3' to 5' exonuclease fiction, which is induced to remove an incorporated labelled base after detection of incorporation. A corresponding non-labelled base may then be incorporated into the complementary strand to allow further sequence determinations to be made. Repeating the procedure allows the sequence of the complement to be identified, and thereby the target sequence also.

The use of the polymerase enzyme's exonuclease function in this way is a characteristic feature of the invention. It permits repeated incorporation of labelled bases to take place, without the requirement for separate steps of chemical cleavage or photoblcaching.

Accordingly, a method for determining the sequence of a target polynucleotide on an array, comprises the steps of:
 (i) contacting the array with one or more detectably-labelled bases A, T, G and C, under conditions that permit the polymerisation reaction to occur, to thereby incorporate a labelled base into a strand complementary to the target;
 (ii) removing non-incorporated bases and detecting an incorporation event;
 (iii) optionally repeating steps (i) and (ii) with one or more additional labelled bases, to determine a partial sequence;
 (iv) contacting the array of step (iii) with a DNA polymerase having 3' to 5' exonuclease activity, under conditions whereby the polymerase cleaves the labelled base(s) and incorporates corresponding non-labelled base(s); and
 (v) repeating steps (i)–(iv) sequentially, to determine the sequence.

Sequencing the polynucleotides on the array makes it possible to form a spatially addressable array. This may then be used for many different applications, including genotyping studies and other characterization experiments.

The method of the present invention may be automated to produce a very efficient and fast sequence determination.

DESCRIPTION OF THE INVENTION

Figure 1:
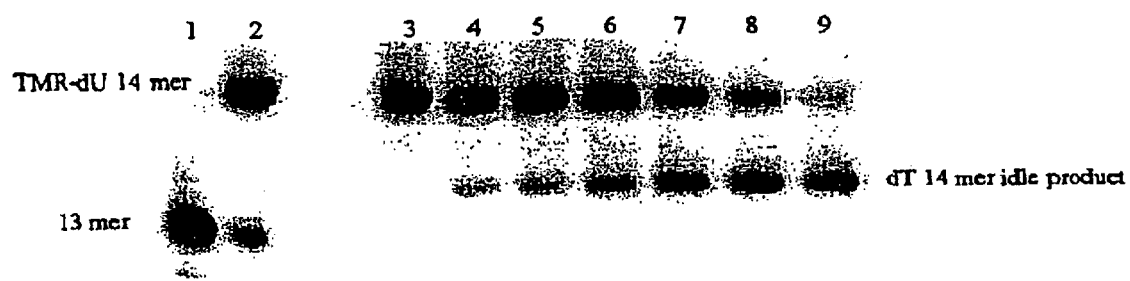
FIG. 1 illustrates the gradual replacement of a terminal labelled base with an unlabelled base, using a polymerase enzyme.

The method according to the invention, for determining the sequence of the arrayed polynucleotides, is carried out by contacting the array separately with the different bases to form the complement to that of the target polynucleotide, and detecting incorporation. The method makes use of polymerisation, whereby a polymerase enzyme extends the complementary strand by incorporating the correct base complementary to that on the target. The polymerisation reaction also requires a specific primer to initiate polymerisation.

For each cycle, the incorporation of a labelled base is carried out by the polymerase enzyme, and the incorporation event determined. Many different polymerase enzymes are now known to comprise an exonuclease function which is used to remove mismatches or mutations during normal DNA replication. This function is exploited in the present invention to remove the incorporated labelled base (or bases) after detection, permitting further sequence determinations to be made.

In the context of the invention, reference to the bases A, T, G and C is taken to be a reference to the deoxynucleoside triphosphates adenosine, thymidine, guanosine and cytidine, and to functional analogs thereof, including the chain termination dideoxynucleoside triphosphates which may be used as the labelled bases for the initial incorporation event.

The terms "arrayed polynucleotides" and "polynucleotide arrays" are used herein to define an array of polynucleotides that are immobilized on a solid support material. The polynucleotides may be immobilized to the solid support through a linker molecule, or may be attached to a particle, e.g. a microsphere, which is itself attached to a solid support material.

The polynucleotides may be attached to the solid support by recognized means, including the use of biotin-avidin interactions. Methods for immobilizing polynucleotides on a solid support are well known in the art, and include lithographic techniques and "spotting" individual polynucleotides in defined positions on a solid support. Suitable solid supports are known in the art, and include glass slides, ceramic and silicon surfaces and plastics materials. The support is usually a flat surface. In one embodiment, the polynucleotides are attached to the solid support via Macroscopic beads (microspheres), which may in turn be attached to the solid support by known means. The microspheres may be of any suitable size, typically in the range of from 10 nm to 100 nm in diameter. Attachment via microspheres allows discrete regions of polynucleotides to be easily generated on the array. Each microsphere may have multiple copies of a polynucleotide attached, and each microsphere can be resolved individually to determine incorporation events. Preferably, the arrays that are used are single molecule arrays that comprise polynucleotides in distinct optically resolvable areas, e.g. as disclosed in WO-A-00/06770.

The sequencing method may be carried out on both single molecule and multi molecule arrays, i.e. arrays of distinct individual molecules and arrays of distinct regions comprising multiple copies of one individual molecule. When multi-molecule arrays are used, it may be preferable to use a mixture of labelled and non-labelled base in the initial incorporation step. Diluting the concentration of labelled base in this way ensures that not every complementary strand incorporates a labelled base, and therefore distinct labels can be resolved within the relatively high densities of the multi molecule arrays. Single molecule arrays allow each individual polynucleotide to be resolved separately. The use of single molecule arrays is preferred. Sequencing single molecule arrays allows a spatially addressable array to be formed.

The term "spatially addressable" is used herein to describe how different molecules may be identified on the basis of their position on an array.

The method makes use of the polymerisation reaction to generate the complementary sequence of the target. The conditions necessary for polymerisation to occur will be apparent to the skilled person.

The polymerase required to carry out the incorporation of the labelled bases into the complementary strand (step (i)) does not need to have an exonuclease function and indeed it is preferred if it does not have this function. The potymerase may be removed from the array by a washing step, and a suitable polymerase, comprising an exonuclease activity, brought into contact with the array in a subsequent step, for example on addition of the non-labelled bases. Suitable polymerase enzymes will be known to those skilled in the art, and include DNA polymerase I, the Klenow fragment, DNA polymerase III and T4 or T7 DNA polymerase.

To carry out the polymerase reaction it will usually be necessary to first anneal a primer sequence to the target polynucleotide, the primer sequence being recognized by the polymerase enzyme and acting as an initiation site for the subsequent extension of the complementary strand. The primer sequence may be added as a separate component with respect to the target polynucleotide. Alternatively, the primer and the target polynucleotide may each be part of one single stranded molecule, with the primer portion forming an intramolecular duplex with a part of the target, i.e. a hairpin loop structure. This structure may be immobilized to the solid support at any point on the molecule.

Other conditions necessary for carrying out the polymerase reaction, including temperature, pH, buffer compositions etc., will be apparent to those skilled in the art.

This polymerisation step is allowed to proceed for a time sufficient to allow incorporation of a base. Bases that are not incorporated are then removed, for example, by subjecting the array to a washing step, and detection of the incorporated labels may then be carried out.

In a preferred embodiment, the label is a fluorescent moiety and may be attached to the base in such a way to prevent further incorporation from occurring, i.e. the base is a chain terminator. Many examples of fluorophores that may be used are known in the prior art e.g. tetramethylrhodamine (TVR). The attachment of a suitable fluorophore to a base can be carried out by conventional means. Suitably labelled bases are also available from commercial sources. When the label is a fluorophore, the fluorescence signal generated on incorporation may be measured by optical means, e.g. by a confocal microscope.

Detection may be by conventional means, for example if the label is a fluorescent moiety, detection of an incorporated base may be carried out by using a confocal scanning microscope to scan the surface of the array with a laser, to image a fluorophore bound directly to the incorporated base. Alternatively, a sensitive 2-D detector, such as a charge-coupled detector (CCD), can be used to visualize the individual signals generated. However, other techniques such as scanning near-field optical microscopy (SNOM) are available and may be used when imaging dense arrays. For example, Using SNOM, individual polynucleotides may be distinguished when separated by a distance of less than 100 nm, e.g. 10 nm to 10 $\mu$m. For a description of scanning near-field optical microscopy, see Moyer et al., Laser Focus World (1993) 29:10. Suitable apparatus used for imaging polynucleotide arrays are known and the technical set-up will be apparent to the skilled person.

After the detection of an incorporation event, the exonuclease activity of the polymerase enzyme is used to remove the labelled base. The polymerase is usually added separately after the washing step which may have removed the polymerase that incorporated the labelled base. The amount of polymerase required will depend on the amount of polynucleotides arrayed on the solid support, but can be determined readily by the skilled person. A suitable concentration will be 10 nM to 10 $\mu$M. In addition to the polymerase, an unlabelled base corresponding to that incorporated may be added. The unlabelled base will not be incorporated onto the complementary strand until removal of the labelled base. The unlabelled base may be a chain-terminator having a removable blocking group or ligand attached. The blocking group must be removed prior to repeating step (i). Suitable blocking groups are known in the art and include photoactivatible ligands.

In the absence of further polymerisation, the polymerase will "switch on" its exonuclease activity to cleave the terminal base on the complementary strand. Cleavage will proceed until a suitable base is available for incorporation, when the more favoured polymerisation reaction will occur. There is therefore an equilibrium reaction occurring with repeated cleavage and (if available) subsequent base incorporation at the terminal end of the complementary strand. Further cleavage, beyond the terminal base, is prevented by the preference of the polymerase for DNA synthesis.

The process of incorporating and removing labelled bases may then be repeated using each of the different bases until the sequence has been determined.

The cleavage/polymerisation steps do not need to be repeated sequentially for each incorporated base. For example, it is possible that several bases are incorporated (and detected) prior to the cleavage step. To illustrate this, the following (template) sequence may be considered.

5'-ATG

3'-TACGTCTAT-5' (SEQ ID NO. 1)

A first labelled base C may be incorporated onto the template, and S incorporation detected. Further labelled bases A and G may then be added sequentially with detection. It will then be known that CAG forms a partial sequence of the growing strand. The labelled bases may then be removed by the exonuclease activity of a polymerase. The exonuclease activity may be induced by incubating the polymerase with the template in the presence of only the non-labelled base C. This base cannot be incorporated onto the template and so the polymerisation reaction "stalls" and is replaced by the exonuclease activity. The labelled bases are removed until cleavage of the labelled C occurs, thereby permitting incorporation of the non-labelled C. The addition of the other non-labelled bases A and G can then be carried out to re-form the growing strand. The procedure may then be repeated for the next part of the template sequence.

The following Example illustrates the invention, with reference to the accompanying drawing.

EXAMPLE

A 20 mer target polynucleotide (SEQ ID NO. 2) and a suitable (13 mer) primer molecule (SEQ ID NO. 3) were used having the sequences:

3'-TGGACGGCTGCGAATCGTC-5' (SEQ ID NO. 2)

5'-ACCTGCCGACGCT-3' (SEQ ID NO. 3)

Incorporation of the fluorescent base (TMR-dUTP; obtained from Nycomed Amersham) was performed in a buffer of 50 mM Tris-HCl, pH 7.5, 10 mM NaCl, 2 mM DTT, 1 mM $K_3PO_4$, 0.1 mM EDTA, and 0.1 mg/ml BSA (100 μl total volume). The 13/20 mer duplex substrate and T4 DNA polymerase (lacking an exonuclease function) were present at final concentrations of 100 nM and 150 nM, respectively. The polymerisation reaction was initiated by addition of a mixture of TMR-dUTP/$MgCl_2$ to final concentrations of 10 μM and 3 mM, respectively. After three minutes, the reaction was heated to 90° C. (to inactivate the enzyme) and cooled slowly to reanneal the duplex.

After reannealing, BSA, dTTP and T4 DNA polymerase (having a 3' to 5' exonuclease function) were added to final concentrations of 0.1 mg/ml, 5 mM, and 500 nM, respectively. The reaction was allowed to proceed at 23° C., and then quenched, at various time points up to 30 minutes, using 0.5 M EDTA.

The reaction mixtures at each time point were resolved by electrophoresis and imaged using a Molecular Dynamics phosphoimager.

The results are shown in FIG. 1. In FIG. 1, lane 1 represents the 13/20 mer standard at t=0; lanes 2 and 3 represent TMR-dUTP incorporation with reaction quenching at t=1 and 3 minutes, respectively; and lanes 4–9 represent quenching at t=1, 3, 5, 10, 20 and 30 minutes, respectively.

It can be seen that, during the time course of the reaction, the amount of labelled 14 mer (the 13 mer and incorporated labelled base) is reduced as the labelled base is excised from the polynucleotide and an unlabelled base incorporated. This represents the "idling" of the polymerase and the "switching on" of the exonuclease function. This demonstrates that the exonuclease activity can be utilized to excise a terminal base and, provided that a suitable replacement base is present, the polynucleotide is maintained, ready for further sequencing to occur.

What is claimed is:

1. A method for determining the sequence of a target polynucleotide on an array, comprising the steps of:

(i) contacting the array with a first DNA polymerase and one or more detectably-labelled bases A, T, G and C, under conditions that permit a polymerisation reaction to occur, to thereby incorporate a labelled base into a strand complementary to the target polynucleotide;

(ii) removing non-incorporated bases and the first DNA polymerase and detecting an incorporation event;

(iii) contacting the array of step (ii) with a second DNA polymerase having 3' to 5' exonuclease activity and non-labelled blocked bases A, T, G and C, under conditions whereby the second DNA polymerase is capable of cleaving one labelled base from the strand complementary to a target polynucleotide and incorporating a corresponding non-labelled blocked base into the strand complementary to the target polynucleotide, thereby replacing the labelled base with a non-labelled blocked base, wherein the non-labelled blocked base comprises a removable blocking group which prevents further base incorporation from occurring;

(iv) removing the removable blocking group from the non-labelled blocked base; and (v) repeating steps (i)–(iv) sequentially, to determine the sequence.

2. A method according to claim 1, wherein each detectably-labelled base is labelled with a different fluorophore.

3. A method according to claim 1, wherein the labelled base is a chain terminator.

4. A method according to any preceding claim 1, wherein detecting in step (ii) is carried out using optical means.

5. A method according to claim 1, wherein the second DNA polymerase is DNA polymerase I, DNA polymerase III, the Klenow fragment, T4 polymerase, or T7 polymerase.

6. A method according to claim 1, wherein the first DNA polymerase is a polymerase lacking exonuclease activity.

7. The method of claim 1, wherein steps (i) and (ii) are repeated with one or more additional detectably-labelled bases, wherein said method determines a partial sequence of the target polynucleotide.

\* \* \* \* \*